United States Patent [19]

Busetto et al.

[11] Patent Number: 5,225,113
[45] Date of Patent: Jul. 6, 1993

[54] PHOTOCHROMATIC COMPOSITION ENDOWED WITH LIGHT FATIGUE RESISTANCE AND PHOTOCHROMATIC ARTICLES WHICH CONTAIN IT

[75] Inventors: Carlo Busetto, San Donato Milanese; Luciana Crisci, Sant Angelo Lodigiano, both of Italy

[73] Assignee: Enichem Synthesis S.p.A., Palermo, Italy

[21] Appl. No.: 853,910

[22] Filed: Mar. 19, 1992

Related U.S. Application Data

[63] Continuation of Ser. No. 475,808, Feb. 6, 1990, abandoned.

[30] Foreign Application Priority Data

Feb. 10, 1989 [IT] Italy ................ 19407 A/89

[51] Int. Cl.$^5$ .................. G02B 5/23; F21V 9/04; C08J 5/35
[52] U.S. Cl. .................. 252/586; 252/589; 524/96
[58] Field of Search ............ 252/582, 586, 589; 524/96

[56] References Cited

U.S. PATENT DOCUMENTS

| | | | |
|---|---|---|---|
| 4,177,186 | 12/1979 | Rody et al. | 260/45.8 N |
| 4,720,356 | 1/1988 | Chu | 252/586 |
| 4,946,880 | 8/1990 | Costanzi et al. | 524/96 |
| 4,968,454 | 11/1990 | Crano et al. | 252/586 |

FOREIGN PATENT DOCUMENTS

| | | |
|---|---|---|
| 0195898 | 10/1986 | European Pat. Off. . |
| 0263561 | 4/1988 | European Pat. Off. . |

Primary Examiner—Robert L. Stoll
Assistant Examiner—Philip Tucker
Attorney, Agent, or Firm—George P. Hoare, Jr.; Shea & Gould

[57] ABSTRACT

A photochromatic composition, endowed with a high light fatigue resistance contains a photochromatic compound belonging to the class of spirooxazines and an U.V.-stabilizer consisting of a sterically hindered amine to be defined by means of formula (I):

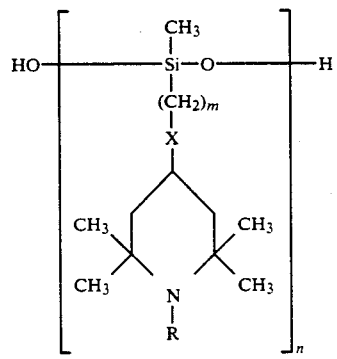

wherein:
R is either hydrogen or a methyl group,
x is either oxygen or nitrogen,
m is a number comprised within the range of from 2 to 10, and
n is a number coprised within the range of from 1 to 100.

A photochromatic article made from a thermoplastic material, endowed with a high light fatigue resistance, contains a thermoplastic material and the hereinabove disclosed photochromatic composition.

6 Claims, No Drawings

PHOTOCHROMATIC COMPOSITION ENDOWED WITH LIGHT FATIGUE RESISTANCE AND PHOTOCHROMATIC ARTICLES WHICH CONTAIN IT

This is a continuation, of application Ser. No. 07/475,808, filed Feb. 6, 1990 now abandoned.

The present invention relates to a photochromatic composition, to the photochromatic articles endowed with light fatigue resistance which contain such a composition, and to the process for preparing said photochromatic articles.

In the art, the need is felt often, of having available articles made from plastic material, which are endowed with photochromatic characteristics, i.e., are capable of reversibly changing their colour and/or their light transmittance when are exposed to light. For this purpose, the organic photochromatic compounds are used, with those organic photochromatic compounds being preferred, which belong to the class of spirooxazines, which are disclosed, e.g., in Can. J. Chem. 61 300 (1983) and in U.S. Pat. Nos. 3,562,172; No. 3,578,602; No. 4,215,010 and No. 4,637,698.

The thermoplastic materials, and, in particular, the thermoplastic organic polymers, are transformed into finished articles by means of the usual techniques of moulding, extrusion, and the like. Under the conditions, and, in particular, the temperature conditions, under which such processes are carried out, the spirooxazines undergo degradation phenomena, or anyway decay phenomena, accompanied by the irreversible development of undesired colours.

According to as disclosed in Italian patent application No. 21,008 A/88 filed on Jun. 17th, 1988 to the same Applicant's name, such a problem can be overcome by adding a nitrogen-containing, basic compound, selected from the group consisting of the acyclic or non-aromatic cyclic amines, amidines and guanidines, in association with the organic photochromatic compound, to said thermoplastic organic polymers, during the step of fabrication thereof.

U.S. Pat. No. 4,720,356 discloses photochromatic compositions endowed with light fatigue resistance which comprise a spirooxazine in combination with a sterically hindered amine, selected from among the amines which are usually employed in order to stabilize the organic polymers against U.V. light.

The present Applicant has found now that particular sterically hindered amines containing silicon in their molecular structure are capable of endowing the photochromatic compounds of spirooxazine type with an extremely high light fatigue resistance. The present Applicant was also able to find that the use of such sterically hindered amines, in association with a photochromatic compound of spirooxazine type makes it possible the phenomena of degradation of said spirooxazine to be prevented, or at least to be substantially reduced, which occur during the high-temperature processing of the thermoplastic organic polymers, and photochromatic articles to be obtained, which are endowed with excellent characteristics of light fatigue resistance.

In accordance therewith, according to a first aspect thereof, the present invention relates to a photochromatic composition, endowed with a high light fatigue resistance, which contains a photochromatic compound belonging to the class of spirooxazines and an U.V.-stabilizer consisting of a sterically hindered amine to be defined by means of formula (I):

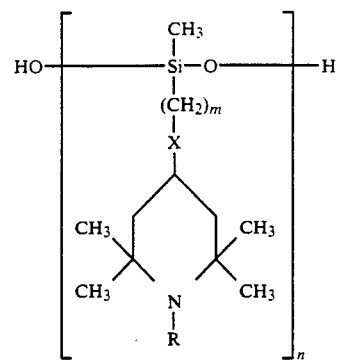

wherein:

R is either hydrogen or a methyl group,

X is either an oxygen or nitrogen atom m is a number comprised within the range of from 2 to 10, and n is a number comprised within the range of from 1 to 100.

Advantageously, in said composition the weight ratio of the photochromatic compound belonging to the class of spirooxazines to the sterically hindered amine is comprised within the range of from 1:0.5 to 1:20, and is preferably comprised within the range of from 1:1 to 1:10.

According to another aspect thereof, the present invention relates to a photochromatic article, made from a thermoplastic material, characterized in that it contains:

(a) a thermoplastic polymer;

(b) a photochromatic compound belonging to the class of spirooxazines; and (c) a sterically hindered amine (I); wherein the (b) component is contained in an amount of from 0.01 to 3 parts by weight and the (c) component is contained in an amount of from 0.05 to 4 parts by weight per each 100 parts by weight of the (a) component. Said photochromatic article preferably contains from 0.01 to 1 parts by weight of component (b) and from 0.1 to 2 parts by weight of (c) component per each 100 parts by weight of (a) component. The weight ratio of the (b) component to the (c) component is generally kept comprised within the range of from 1:0.5 to 1:20, and preferably of from 1:1 to 1:10.

The thermoplastic polymers useful for the intended purpose are polyolefins, such as polyethylene (low-density polyethylene and high-density polyethylene, and low-density, linear polyethylene) and polypropylene, polyvinyl chloride, plasticized polyvinyl chloride, ethylene-vinyl acetate copolymers (EVA), polyvinyl acetate, cellulose acetate, cellulose acetate-butyrate, (meth)acrylic resins, polystyrene, polycarbonate, polyamides and linear polyesters (such as polyethylene terephthalate and polybutylene terephthalate).

The photochromatic compounds belonging to the class of spirooxazines, useful for the intended purpose, are compounds which can be defined by means of the general formula (II):

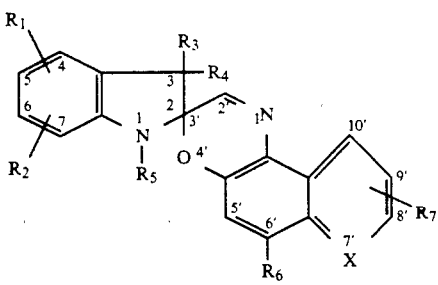

wherein:

R₂ and R₂ represent, independently from each other, a hydrogen atom or a halogen atom (fluorine, chlorine, bromine) or a group selected from among linear or branched $(C_1-C_5)$-alkyl or $(C_1-C_5)$-haloalkyl, $(C_1-C_5)$-alkoxy, nitro or cyano groups;

R₃ and R₄ represent, independently from each other, a linear or branched $(C_1-C_5)$-alkyl, a phenyl or a benzyl group; or R₃ and R₄ represent, jointly and together with the carbon atom to which they are bonded, a $(C_5-C_8)$-cycloalkyl group;

R₅ represents a linear or branched $(C_1-C_5)$-alkyl, a phenyl, a benzyl or an allyl group;

R₆ represents the hydrogen atom or a linear or branched $(C_1-C_5)$-alkyl group, or an —NR₈R₉ group, wherein R₈ is a linear or branched $(C_1-C_5)$-alkyl group, a phenyl or a benzyl group, R₉ is a hydrogen atom, or has the same meaning as of R₈, or R₈ and R₉, as considered jointly and together with the nitrogen atom they are bonded to, form a cyclic structure of from 5 to 12 members, possibly containing a further heteroatom selected from among oxygen and nitrogen;

R₇ represents a hydrogen atom or a halogen atom (fluorine, chlorine, bromine) or a group selected from among linear or branched $(C_1-C_5)$-alkyl or $(C_1-C_5)$-haloalkyl, $(C_1-C_5)$-alkoxy, cyano groups, alkylthio groups, carboxy ester groups containing from 1 to 5 carbon atoms in their ester moiety, or represents a condensed aromatic or heterocyclic ring; and X represents either CH or N.

In particular, the R₁ and R₂ groups, when are different from hydrogen atom, can be linked to a whatever one of the 4, 5, 6 and 7-positions of the indolinic moiety of the molecule. Furthermore, the R₇ group, when it does not represent a hydrogen atom or a condensed aromatic or heterocyclic ring, can be in any one of 7', 8', 9' and 10' positions of the naphthenic moiety of the molecule.

Examples of photochromatic compounds belonging to the class of spirooxazines are:

1,3,3,4,5- or 1,3,3,5,6-pentamethyl spiro-{indolino-2,3'-[3H]-naphtho-(2,1-b)-(1,4)-oxazine};

1,3,3-trimethyl spiro-{indolino-2,3'-[3H]-naphtho-(2,1-b)-(1,4)-oxazine};

1,3,3-trimethyl-6'-piperidino spiro-{indolino-2,3'-[3H]-naphtho-(2,1-b)-(1,4)-oxazine};

1,3,3-trimethyl-6'-morpholino spiro-{indolino-2,3'-[3H]-naphtho-(2,1-b)-(1,4)-oxazine};

1,3,3,4,5- or 1,3,3,5,6-pentamethyl-6'-piperidinospiro-{indolino-2,3'-[3H]-naphtho-(2,1-b)-(1,4)-oxazine}; and 1,3,3-trimethyl-6'-piperidino-9'methoxy spiro-{indolino-2,3'-[3H]-naphtho-(2,1-b)-(1,4)-oxazine}.

The sterically hindered amines (I) are disclosed in the U.S. Pat. No. 103,961, filed on Oct. 5, 1987 to the same Applicant's name.

The photochromatic articles according to the present invention can be obtained by submitting to hot-processing mixtures consisting of the (a), (b) and (c) components, possibly containing one or more additive(s) selected from the group consisting of inert fillers, plasticizers, pigments, lubricants, antistatic agents, slipping agents, antiblocking agents, and the like. The hot-processes are those which are customarily used in the fabrication of the thermoplastic materials, and comprise melt-processing or plastic-state processing techniques, such as extrusion, spinning, compression-moulding, injection-moulding, blowing, calendering, reaction injection moulding (RIM) and still others, which are normally carried out within a temperature range of from about 100° C. up to about 300° C. In this way, articles such as films, fibres, tapes, sheets, contoured pieces, containers, protecting filters, technical articles, toys, fabrics, and so forth, are obtained, which are not affected by the phenomena deriving from the degradation of the photochromatic compound, and are capable for preserving their photochromatic characteristics within the photochromatic manufactured article for unexpectedly long time periods, as compared to the effects caused by the amines used in the prior art.

The following experimental examples are reported for the purpose of better illustrating the present invention.

In said examples, the following photochromatic substances are used as the (b) component:

(b-1) 1,3,3,4,5- and 1,3,3,5,6-pentamethyl spiro-{indolino-2,3'-[3H]-naphtho-(2,1-b)-(1,4)-oxazine};

(b-2) 1,3,3-trimethyl-6'-piperidino spiro-{indolino-2,3'-[3H]-naphtho-(2,1-b)-(1,4)-oxazine}:

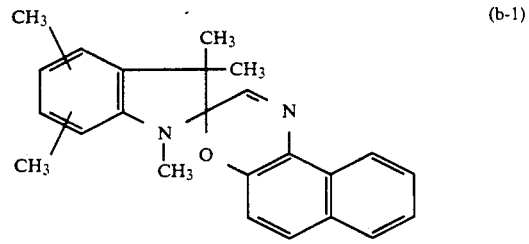

(b-1)

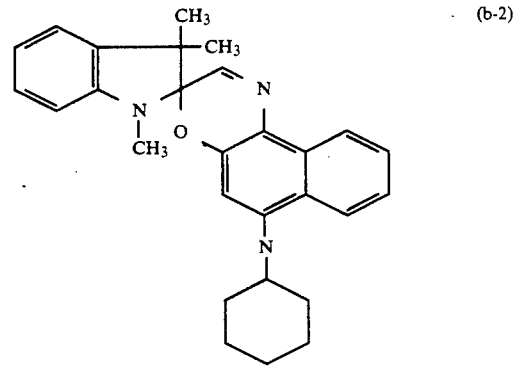

(b-2)

Furthermore, the following sterically hindered, either secondary or tertiary, amines are used as the (c) component:

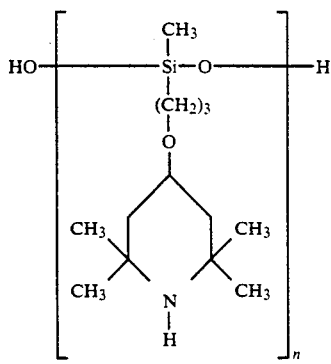

(wherein the average value of n is of about 8);
(c-2) TINUVIN 770 (A commercial product manufactured by Ciba Geigy);
(c-3) CHIMASSORB 944 (A commercial product manufactured by Ciba Geigy);

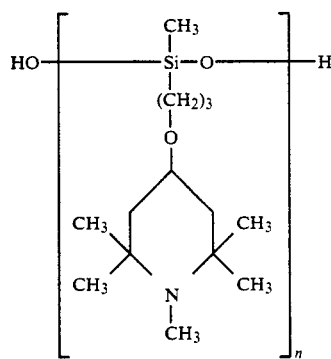

(wherein the average values of n is of about 8); and
(c-5) TINUVIN 622 (A commercial product manufactured by Ciba Geigy).

Said (b) and (c) components are added to a range of organic polymers, and the so obtained mixtures are transformed into photochromatic manufactured articles. In particular, photochromatic slabs and films of polyethylene, polypropylene and ethylene-vinyl acetate copolymer (EVA) are respectively obtained by injection-moulding and extrusion, and photochromatic slabs of plastisol PVC are prepared by gelling at 190° C., with the photochromatic product being dissolved is a plasticizer (dioctyl phthalate), and with said solution being added to said plastisol PVC in suitable proportions.

On the so-obtained photochromatic articles, the following characterization is carried out:

UV-visible spectrum, as determined by a Cary 2300 spectrophotometer, in reflectance mode with integrating sphere for opaque or translucid materials, such as plastisol PVC, polyethylene and polypropylene slabs. The optical density, as measured at the wavelength of maximum absorption of the mixture in its deactivated form is taken as the measure of the concentration, or of the residual concentration, of the photochromatic compound in the sample.

Change in light transmittance ($\Delta Y$) at 23° C., as determined by means of a MAC-BETH spectrophotometer after a 120-seconds-long activation by means of an UV-A lamp of 9 W/m$^2$ of irradiance in case of transparent materials (polyethylene, polypropylene, EVA films).

Kinetic of return to the deactivated form (time of recovery of 50% of initial transmittance, $t_{\frac{1}{2}}$), by means of a MAC-BETH spectrophotometer under the same activation conditions as above.

Resistance to accelerated ageing, defined as the persisting of the photochromatic activity over time, as determined by means of an Atlas Weather-O-Meter (WOM) equipped with a continuous-irradiation xenon lamp of 6,500 W operating at a temperature of 63° C. at the black reference panel, and at a relative humidity of 50%. The ageing resistance is evaluated by measuring, after various times of exposure in the WOM, the values of optical density at $\lambda_{max}$ of the deactivated form whenever possible, and the residual $\Delta Y$ after activation by means of the UV-A lamp.

Example 1

Four mixtures are prepared (mixtures Nos. 1-4 in Table 1), which are constituted by a polypropylene powder, MOPLEN FLF 20 brand by HIMONT, with a fluidity degree of 11, by the photochromatic product (b-2) and by the (c) component as shown in said Table 1, in the mutual weight ratio of 100:0.1:0.25.

TABLE 1

| Mixture No. | 1 | 2 | 3 | 4 |
|---|---|---|---|---|
| (c) Component | — | c-1 | c-2 | c-3 |

Test mixture No. 1 does not contain any (c) component, and is the comparative test. In test mixtures No. 3 and No. 4, sterically hindered amines are used, which are different from the sterically hindered amines as provided according to the compositions of the present invention; therefore, they are comparative test mixtures.

The so prepared mixtures are transformed into films of 50 μm of thickness by extrusion at the temperature of 215° C. The photochromatic characteristics of these films, and their ageing resistance in WOM, as evaluated under the above indicated conditions, are reported in Table 2. The data reported in Table 2 efficaciously shows the stabilizing effect of the (c) component according to the instant invention, both during the processing step, and in terms of ageing resistance. In particular, test mixture No. 2 shows higher values of photochromatic activity and of ageing resistance, than as shown by test mixtures Nos. 1, 3 and 4.

TABLE 2

| Test No. | 1 | 2 | 3 | 4 |
|---|---|---|---|---|
| Optical density in the deactivated state (363 nm) | 0.169 | 0.180 | 0.172 | 0.141 |
| Colour in the deactivated state | greenish | colourless | colourless | colourless |
| Colour in the activated state | violet | red/violet | red/violet | red/violet |
| $\Delta Y$, 23° C. | 18.4 | 22.3 | 20.8 | 16.7 |
| $t_{\frac{1}{2}}$, 23° C. | 22 sec | 21 sec | 21 sec | 16 sec |
| Resistance to ageing in WOM (after 30 hours) | | | | |
| Optical density | about 0 | 0.109 | 0.080 | 0.071 |
| $\Delta Y$ | 0 (15 h) | 5.1 | 1.4 | 1.2 |

EXAMPLE 2

The mixtures Nos. 5 and 6 are prepared in the same way as disclosed in Example 1, with the same mutual proportions of the components, with different (c) components being used, as shown in Table 3. Test 6 is a comparative test.

TABLE 3

| Mixture No. | 5 | 6 |
|---|---|---|
| (c) Component | c-4 | c-5 |

These mixtures are transformed into photochromatic films of 50 μm of thickness, which are evaluated in the same way as of Example 1.

Their characteristics are reported in Table 4.

TABLE 4

| Test No. | 5 | 6 |
|---|---|---|
| Optical density in the deactivated state (363 nm) | 0.150 | 0.147 |
| Colour in the deactivated state | colourless | colourless |
| $\Delta Y$, 23° C. | 17.3 | 13.6 |
| $t_{\frac{1}{2}}$, 23° C. | 14 sec | 15 sec |
| Resistance to ageing in WOM (after 15 hours) | | |
| Optical density | 0.109 | 0.096 |
| $\Delta Y$ | 9.8 | 7.5 |

EXAMPLE 3

By operating in the same way as of Example 1, the following mixtures from 7 to 12 are prepared according to as reported in Table 5, with the compound (c-1) being used as the (c) component, at different concentrations. Test mixture No. 7, which does not contain the (c) component, is a comparative Test.

TABLE 5

| Mixture No. | 7 | 8 | 9 | 10 | 11 | 12 |
|---|---|---|---|---|---|---|
| (c-1) Component (phr) | 0 | 0.10 | 0.20 | 0.25 | 0.50 | 1.0 |

These mixtures are transformed into photochromatic films of 50 μm of thickness, which are evaluated in the same way as of the preceding example. The photochromatic characteristics of the films are reported in Table 6.

TABLE 6

| Test No. | Optical density in deactivated state (363 nm) | $\Delta Y$ (at 23° C.) | $t_{\frac{1}{2}}$ (23° C.) | Resistance to ageing in WOM | |  | |
|---|---|---|---|---|---|---|---|
| | | | | After 15 hours | | After 30 hours | |
| | | | | Optical Density | $\Delta Y$ | Optical Density | $\Delta Y$ |
| 7 | 0.169 | 18.4 | 22 seconds | 0 | 0 | — | — |
| 8 | 0.225 | 28.6 | 24 seconds | 0.127 | 12.5 | 0.055 | 1 |
| 9 | 0.233 | 24.8 | 20 seconds | 0.127 | 11.2 | 0.043 | 1.5 |
| 10 | 0.180 | 22.3 | 21 seconds | 0.144 | 12.9 | 0.109 | 5.1 |
| 11 | 0.147 | 17.5 | 19 seconds | 0.110 | 10.9 | 0.062 | 3.2 |
| 12 | 0.119 | 16.9 | 19 seconds | 0.084 | 9.6 | 0.035 | 2.1 |

The data reported in Table 6 shows that the most suitable concentration of the (c) component is of around 0.25 phr.

Example 4

The following mixtures Nos. 11 and 12 are prepared, which are constituted by polypropylene powder, MOPLEN FLF20 brand by HIMONT, the photochromatic compound (b-1) and the component (c-1), in the mutual ratios as shown in Table 7.

TABLE 7

| Mixture No. | 12 | 13 |
|---|---|---|
| Polypropylene FLF 20, phr | 100 | 100 |
| Photochromatic compound (b-1), phr | 0.1 | 0.1 |
| Component (c-1) | 0 | 0.25 |

The mixture No. 12, which does not contain any (c) component, is reported for comparative purposes.

The photochromatic films of 50 μm of thickness, obtained from these mixtures, display the characteristics as reported in Table 8.

TABLE 8

| Test No. | 5 | 6 |
|---|---|---|
| Colour in the deactivated state | light blue | colourless |
| Optical density in the deactivated state | 0.100 | 0.117 |
| Colour in the activated state | blue-violet | blue-violet |
| $\Delta Y$, 23° C. | 4.2 | 4.8 |
| $t_{\frac{1}{2}}$, 23° C. | 10 sec | 9 sec |
| Resistance to ageing in WOM (after 15 hours) | | |
| Optical density | 0.080 | 0.107 |
| $\Delta Y$ | 0.3 | 4.0 |

EXAMPLE 5

The mixtures Nos. 14, 15 and 16 are prepared. These mixtures are constituted by an ethylene-vinyl acetate copolymer (EVA), RIBLENE D brand by ENICHEM, with vinyl acetate = 19% and fluidity degree 3, the photochromatic compound (b-2) and the (c) component as reported in Table 9, in the mutual ratio of 100:0.1:0.25 by weight.

TABLE 9

| Mixture No. | 14 | 15 | 16 |
|---|---|---|---|
| (c) Component | — | c-1 | c-2 |

These mixtures are transformed into photochromatic slabs of 3 mm thickness, by injection moulding at the temperature of 175° C. At the end of the processing, the slab obtained from the mixture No. 15 shows higher photochromatic characteristics and better properties of ageing resistance, than the comparative mixtures Nos. 14 and 16, as shown by the data reported in following Table 10.

TABLE 10

| Test No. | 14 | 15 | 16 |
|---|---|---|---|
| Colour in the deactivated state | colourless | colourless | colourless |

TABLE 10-continued

| Test No. | 14 | 15 | 16 |
| --- | --- | --- | --- |
| Optical density in deactivated state (388 nm) | >4500 | >4500 | >4500 |
| ΔY | 68.6 | 67.6 | 60.9 |
| Resistance to ageing in WOM (after 99 hrs) | | | |
| Optical density | 1.593 | 3.433 | 2.675 |
| ΔY | 31 | 61.6 | 51.4 |

Example 6

The liquid mixtures Nos. 17, 18 and 19 are prepared, which are constituted by PVC plastisol, the photochromatic component (b-1) and the (c) component, as reported in Table 11, in the mutual weight ratio of 100:0.1:0.25.

TABLE 11

| Mixture No. | 17 | 18 | 19 |
| --- | --- | --- | --- |
| (c) Component | — | c-1 | c-2 |

The PVC plastisol already contains conventional stabilizers known from the prior art. The liquid mixtures are cast into glass moulds bounded by a flexible gasket made from an ethylene-vinyl acetate copolymer, and the filled moulds are left standing inside an oven at 190° C. in order to cause the mixture tu turn into the solid state, by gelling.

At the end of the thermal treatment, slabs of plasticized PVC of 3 mm of thickness are obtained, the photochromatic activity of which is evaluated also after ageing inside WOM, by means of the determination of ΔY under the hereinabove reported conditions.

The results obtained are reported in Table 12, wherein Tests 17 and 19 are comparative tests.

TABLE 12

| Test No. | 17 | 18 | 19 |
| --- | --- | --- | --- |
| Colour in the deactivated state | pale green | pale green | pale green |
| ΔY (initial value) | 24.2 | 25.0 | 24.9 |
| ΔY (after 32 hrs. in WOM) | 12.3 | 24.8 | 20.0 |

We claim:

1. A photochromatic composition having high resistance to light fatigue comprising a spirooxazine photochromatic compound and an U.V.-stabilizer having a sterically hindered amine of the formula:

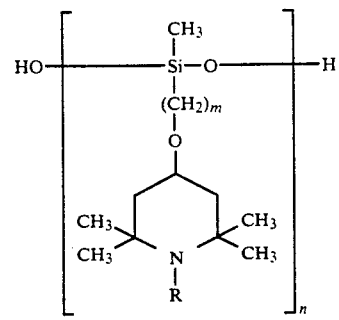

wherein:
R is hydrogen or a methyl group,
m is a number within the range of from 2 to 10, and
n is a number within the range of from 1 to 100.

2. The composition according to claim 1, wherein the spirooxazine photochromatic compound and the sterically hindered amine are present in a weight ratio within the range of from 1:0.5 to 1:20.

3. The composition according to claim 2, wherein said ratio is within the range of from 1:1 to 1:10.

4. A photochromatic article having high resistance to light fatigue comprising:
(a) a thermoplastic polymer;
(b) a spirooxazine photochromatic compound; and
(c) a sterically hindered amine of the formula:

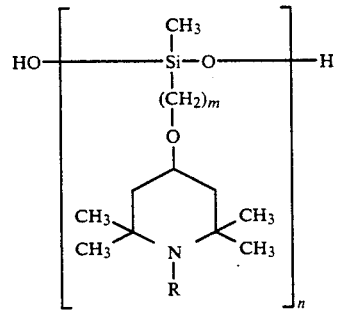

wherein:
R is a hydrogen or a methyl group,
m is a number within the range of from 2 to 10, and
n is a number within the range of 1 to 100,
wherein component (b) is present in an amount of from 0.01 to 3 parts by weight and component (c) is present in an amount of from 0.05 to 4 parts by weight per 100 parts by weight of component (a), and wherein the weight ratio of component (b) to the component (c) is within the range of from 1:05 to 1:20.

5. The photochromatic article according to claim 4, wherein component (b) is present in an amount of from 0.01 to 1 part by weight and component (c) is present in an amount of from 0.1 to 2 parts by weight per 100 parts by weight of component (a) and wherein the weight ratio of component (b) to component (c) is within the range of from 1:1 to 1:10.

6. The photochromatic article according to claim 4 further comprising at least one additive selected from the group consisting of inert fillers, plasticizers, pigments, lubricants, antistatic agents, slipping agents, and antiblocking agents.

* * * * *